United States Patent [19]

Berger et al.

[11] Patent Number: 4,863,453

[45] Date of Patent: Sep. 5, 1989

[54] STERILE CLOSURE DEVICE

[75] Inventors: Richard A. Berger, Troy; Richard A. Burkholder, St. Charles, both of Mo.

[73] Assignee: Sherwood Medical Company, St. Louis, Mo.

[21] Appl. No.: 136,698

[22] Filed: Dec. 22, 1987

[51] Int. Cl.[4] ............ A61M 5/00

[52] U.S. Cl. ............ 604/415; 215/249; 128/764

[58] Field of Search ............ 604/415, 403, 411; 128/763, 764; 215/246, 247

[56] References Cited

U.S. PATENT DOCUMENTS

| | | | |
|---|---|---|---|
| 2,081,138 | 5/1937 | Andersen et al. | 215/83 |
| 2,629,379 | 2/1953 | Fields | 604/415 |
| 2,734,649 | 2/1956 | Callahan et al. | 215/249 |
| 2,783,908 | 3/1957 | Winfield | 215/37 |
| 2,876,775 | 3/1959 | Barr, Sr. et al. | 128/764 |
| 3,480,171 | 11/1969 | Rohde | 215/46 |
| 4,227,617 | 10/1980 | Albrecht et al. | 215/251 |
| 4,294,367 | 10/1981 | Otsuka et al. | 215/246 |
| 4,301,936 | 11/1981 | Percarpio | 215/247 |
| 4,390,104 | 6/1983 | Cummings | 215/232 |
| 4,471,879 | 9/1984 | Connor et al. | 215/249 |
| 4,482,071 | 11/1984 | Ishiwatari | 215/255 |
| 4,538,740 | 9/1985 | Petersen, Jr. | 215/246 |

*Primary Examiner*—Stephen C. Pellegrino
*Attorney, Agent, or Firm*—Stanley N. Garber; Andrew J. Beck; Charles Smith, Jr.

[57] ABSTRACT

A sterile closure device for a stoppered container which includes a cover member positioned over the top portion of the stopper, a shrinkable band member enclosing a peripheral portion of the cover member and the top portion of the stopper and having a pull tab portion by which the band member can be fractured and a spot of adhesive connecting the peripheral portion of the cover member to the band member such that upon fracture of the band member the cover member and tab portion will be removed together.

14 Claims, 1 Drawing Sheet

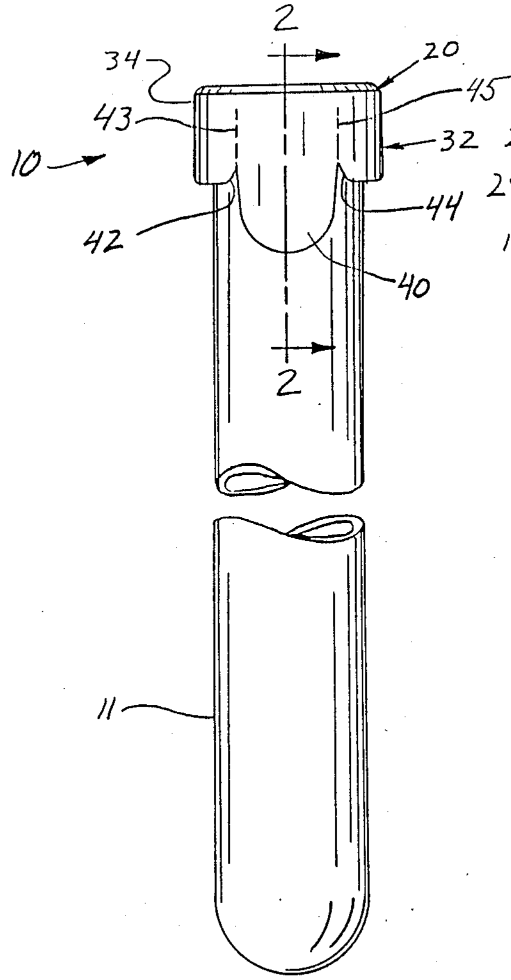
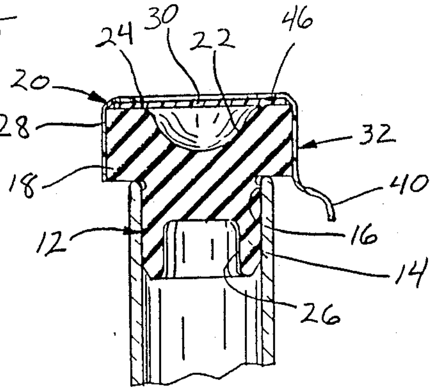
Fig. 2
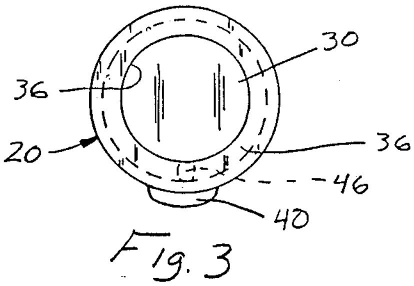
Fig. 3
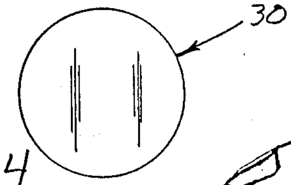
Fig. 4
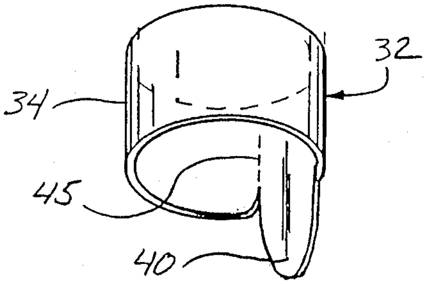
Fig. 5
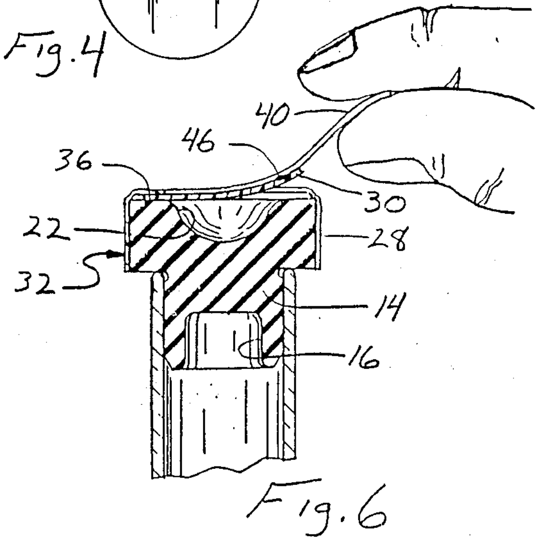
Fig. 6

STERILE CLOSURE DEVICE

The present invention relates to sterile closures for containers and the like and more particularly to sterile closures for containers where the closure and container are sterilized and where the cover can be readily and rapidly removed so that the container is readily made available for use.

Many medicaments and medical accessories today are made available in pre-sterilized form and with pre-sterilized packaging. This has been particularly true in recent years with the advent of pre-measured dosage regimens for hospital pharmacies and medical supply rooms. Many types of medicaments, and particularly those in liquid form, are supplied in sterile containers designed to maintain sterility of the contents even after use. This includes, among many others, biologicals such as vaccines, dyes and tracer solutions and injectables of all types. Most accessory medical and test equipment is now supplied pre-sterilized and in packaging designed for single and multiple usage, particularly small and relatively inexpensive items.

An item used in large quantities in hospitals, medical offices and laboratories are blood collection or sample tubes. Blood sample tubes are designed to contain blood samples and to maintain them in an uncontaminated state. Such tubes are often supplied partially evacuated or at a low vacuum with secure stoppers in place, the whole item being pre-sterilized. Blood sample tubes are designed for reception through their stoppers of a cannula or needle which pierces the stopper to introduce the blood sample therein. In most instances where a medicament is to be administered or a blood sample is to be taken and deposited in a sample tube or container, ease and convenience, while maintaining sterility, are critically important. Making such devices fail safe is also an important requirement since such devices are often used in emergency situations and by persons of widely varying skills and experience.

One type of sterile packaging or sterile closure frequently employed with single and multiple dose injectable medicaments, as well as with containers for receiving blood samples, includes a stopper closing the container, a layer of material placed on the upper end of the stopper, and then an outer band, collar or cover is applied that may protect any exposed part of the stopper as well as the layer of material or any other protective layer applied thereto. The protective layer may be a disc-shaped member which is placed on the container in position to cover over or seal certain portions of the stopper such as the needle pierceable portions. With such known devices it is usually necessary for the user to remove the outer collar or band and then to also separately remove the disc-shaped member to ready the container for receipt of a cannula or syringe needle for the transfer to or from the container of a medicament or blood sample. This requires separate operations by the user, namely, first removal of the collar, and thereafter removal or severance of the disc-shaped member which may require a separate tool. It is the purpose of the present invention to teach the construction of improved closure means which reduce the number of operations necessary to remove them and yet to provide all of the advantages of having a separate closure member held in sealed and sterile engagement with the container or stopper.

The present invention resides in a novel sterile closure device which includes a cover member positioned over at least a portion of a stopper of a container or test tube and a heat shrinkable band member which, after shrinking, will maintain the cover member in its sealed condition on the stopper. The present device also includes a fracturable pull tab on the shrink-on member, and it includes a spot of adhesive positioned between the heat shrinkable member and a surface of the cover member adjacent to the periphery thereof and in substantial alignment with the pull tab. This is done so that when the fracturable pull tab is pulled to break the heat shrunk member it simultaneously pulls the cover member off the stopper thereby obviating the necessity of a separate removal operation. This simplifies the removal operation and makes it possible to remove all of the parts in a single operation, without tools or fingernails, and contributes to maintaining the sterile condition of the stopper until ready for use.

It is a principal object of the present invention to provide improved sterile closure means for medical and other containers and their stoppers.

Another object is to provide sterile closure means which are removable by a single operation.

A further object is to make it easier and quicker to remove the sterile closure means used to cover the stopper on a container.

Another object is to provide a relatively inexpensive easily removable sterile closure means for use on sterile containers and their stoppers.

Another object is to make it possible to remove a multi-part closure in a single operation.

Another object is to make containers used for medical and other purposes easier to use and more fail safe.

These and other objects advantages of the present invention will become apparent to those skilled in the art after considering the following detailed specification in conjunction with the accompanying drawing.

DESCRIPTION OF THE DRAWING

FIG. 1 is a front elevational view of a sample tube having closure means thereon constructed according to the teachings of the present invention;

FIG. 2 is a cross-sectional view taken along line 2—2 of FIG. 1;

FIG. 3 is a top plan view of the closure means of FIGS. 1 and 2;

FIG. 4 is a top view of a disc-like member employed in the present construction;

FIG. 5 is a perspective view of the heat shrinkable band portion of the subject closure means shown in a non-shrunk condition; and FIG. 6 shows the subject closure means being taken off of the stopper on the container.

DESCRIPTION OF THE PREFERRED EMBODIMENT

Referring to the drawing and more particularly by reference numerals, number 10 in FIG. 1 refers to a container which may be a medicine container or test tube, and is shown as a blood collection tube. Container 10 includes a tube such as a conventional glass tube 11 having a closed end and an open end closed by a stopper 12. The stopper 12 is shown in FIG. 2 having a reduced diameter stem portion 14 fitting into the opening 16 of the container 10, and an integral head portion 18 of greater diameter than the open end of container 10 and on which the subject closure means 20 are shown installed. The particular stopper 12 shown is constructed of a material that is pierceable by a metal cannula or needle (not shown) such as might be used to extract substances from the container 10 or introduce substances such as a blood sample into it. Stopper 12 may be made of a suitable needle penetratable self-sealing rubber or rubber-like material used in conventional blood collection tubes. To this end, the stopper 12 is shown having a depression 22 in its outer or top surface 24 and a recess or cavity 26 extending into the opposite inner end. The reduced diameter portion 14 is of a size to be sealably inserted into the container opening 16. The depression 22 and the cavity 26 are constructed to facilitate accurate, fail safe, insertion of the cannula or needle through the stopper 12 and into the container.

The present invention resides primarily in novel closure means 20 for container 10 for sealably covering and closing the outer or upper end surface 24 and sidewall 28 of the stopper head portion 18 and to maintain these portions of the stopper including the depression 22 in a sterile condition until the device is ready to be used.

The closure means 20 includes a cover member 30 shown as a round disc-like member and a closure member or collar 32 connected to cover stopper 12 and at least a portion of the cover member 30.

The cover member 30 is circular and has a diameter slightly less than the diameter of the upper end surface 24 but which covers the recess 22. It is preferably made of a relatively hard material which is substantially non-pierceable by a pointed needle or cannula. Cover member or disc 30 may be made of a hard plastic or metal. For example, it may be made of a styrene material that is 0.015 inch in thickness.

The closure member 32 is made of a shrinkable material such as from a conventional heat shrinkable polyvinyl chloride (PVC). It may, for example, be formed from tubing which is then die cut into a collar having the cylindrical shape shown in FIG. 5. The heat shrinkable material may be, for example, 0.002 inch thick PVC. The collar member 32 has a continuous sidewall 34 and tear tab 40 which extends downwardly from the sidewall 34 of the collar. The sidewall 34 is also shown with notches, one on each opposite side of the tab 40 and indicated at 42 and 44 to facilitate starting the tearing of the tab 40 at least partially from collar 32 when the tab 40 is grasped and pulled as shown in FIG. 6. Tear lines of weakness which respectively include notches 42 and 44 may also respectively include, for example, lines or perforations 43 and 45 shown extending vertically and connecting with each tab notch but the lines of perforations stop at a point below the disc-like member 30 to preserve sterility.

In assembling container 10, the stopper 12 may be inserted into tube 11 while both are in a partially air evacuated chamber to provide the container with a predetermined negative pressure or partial vacuum. The cover member 30 may then be positioned on top of stopper 12, so that it covers recess 22. Then, the collar member 32, such as in the form shown in FIG. 5, is placed over the stopper head 18 with an upper end portion of the collar member extending beyond the upper end surface 4 of the stopper and with the finger tab 40 extending downwardly. A spot of an adhesive 46 (FIGS. 2 and 3) is applied on the top of cover member 30 adjacent its margin as will be discussed hereafter. Heat is applied to the collar 32 to shrink the collar tightly about the sidewall 28 of the stopper 12 and a marginal area of the upper surface of the cover member 30 to form a flange 36 extending over and tightly engaging the marginal area of the upper exterior surface of the cover member for 360° around the cover member. The flange 36 covers the adhesive spot to thereby fixedly connect the collar 32 to the cover member 30. After the container 10 is completely assembled, it can be sterilized in its entirety, such as by radiation sterilization, preferably by gamma radiation.

The spot 46 of adhesive is preferably at a location centered on the tab 40, but this is not essential as the structure generally functions with the adhesive spot anywhere about the periphery of disc 30. The location of the adhesive connection formed by the spot 46 means that when the tab 40 is pulled to sever the collar 32, starting at one or both of the notches 42 and 44, the tab 40 will also operate, when pulled far enough and because of the location of the adhesive spot 46, to pull up on the edge portion of the disc 30, lifting it off of the stopper 12. As the tab 40 is continued to be pulled the disc 30 will continue to be separated from the stopper 12 until the severed tab portion of the collar 32 and the disc 30 come completely free of the stopper with the remaining portion of collar 32 usually still attached to one side of tab 40. By the time the tab 40 has been pulled far enough to break the collar 32 the rest of the collar 32, if not still attached to tab 40, will be loose enough to easily come off. The removal of the tab 40 and the disc 30 can be accomplished in one continuous operation and with the tab 40 remaining attached to the disc 30 so that they come off together. The remaining part of the collar 32, as stated, will have been broken, but usually still partially attached to tab 40. If not still attached it will either fall off or can be easily removed. Usually and preferably, the tab 40 is pulled at a slight angle to the vertical axis of container 10 which ensures that one side of the tab tears through the collar 32 and flange 36 while the collar is connected to the other side of the tab so that the closure 20 usually comes off the container in its entirety when the tab 40 is pulled.

The collar 32 is preferably constructed of a heat shrinkable plastic material, and when positioned on the stopper 12 as shown, and subjected to heat, will shrink-fit itself onto the stopper and in so doing will also press down on the peripheral edge of the disc 30 to maintain it in a sealed and sterile condition on the stopper 12 after a sterilization treatment.

The subject closure means can be applied to the tops of various types of containers, and/or to stoppers and in all cases will operate as described.

It is contemplated to place the disc 30 as a separate piece on the container or stopper or to attach it to the collar member 32 prior to positioning the assembly on a container or stopper. If the members 30 and 32 are not attached to each other prior to installation then a dot of adhesive 46 should be placed on the disc 30 or on the collar 32 at the appropriate location prior to heat shrinking the collar, and the adhesive in any case should be selected to withstand the heat required to shrink the collar 32. In fact the adhesive may be selected to be cured during the heat shrinking or the sterilization process to complete the bond between the disc 30 and the collar 32. Under actual test it has been found that the amount of adhesive applied between the disc 30 and the collar 32 is important. Generally a relatively small amount of adhesive is most desirable as too much adhesive may cause some adhesive migration which could cause the disc 30 to be undesirably adhesively attached to the stopper (or container). On the other hand too little adhesive may prevent the disc 30 from being adaquately attached to the collar 32. Hence limiting the size and amount of adhesive in the deposited dot 46 is important.

Thus there has been shown and described a novel sterile closure device which fulfills all the objects and advantages sought therefor. It will be apparent to those skilled in the art, however, that many changes, modifications, variations and other uses and applications of the subject closure means are possible and contemplated. All such changes, modifications, variations and other uses and applications which do not depart from the spirit and scope of the invention are deemed to be covered by the invention which is limited only by the claims which follow.

What is claimed is:

1. A medical container assembly comprising a container open at one end and closed at the other end, a needle-pierceable stopper closing said open end and having an inner portion in said container and an external portion external to said container, a cover member of a material which is substantially non-pierceable by a needle disposed on the exterior end of said stopper, and a collar of heat shrinkable plastic material heat shrunk over a peripheral surface of said external portion of said stopper in tight fitting relation therewith and with at least a marginal portion of the exterior side of said cover member but not with said container, said collar member including an accessible tab portion that can be pulled to sever said collar member to remove it from said stopper, and means forming a connection between said cover member and said collar member whereby the cover member will separate from said stopper when said tab portion is pulled to sever said collar member.

2. The medical container assembly of claim 1 wherein said means forming a connection include an adhesive.

3. The assembly of claim 1 wherein said cover member is a disc-like member of a material that is of relatively hard plastic.

4. The medical container assembly of claim 1 wherein said cover member is a disc-like member, and the outer diameter of said external portion of said stopper is greater than that of said open end of said container.

5. The medical container of claim 1 wherein the outer diameter of said external portion of said stopper is at least as great as the outer diameter of said cover member.

6. A blood collection tube comprising a blood collection container open at one end and closed at the other end, a needle-pierceable stopper extending into and closing said one end and having a head extending exteriorly of said one end and having an outer diameter greater than the outer diameter of said one end, a disc-like cover member of a material which is substantially non-pierceable by a needle disposed on the exterior end of said head and having an outer diameter not greater then the outer diameter of said head, and a collar member of severable heat shrinkable plastic material tightly encircling and engaging the sidewalls of said head and tightly engaging at least a peripheral portion of the exterior side of said disc-like member entirely around said disc-like member, said collar member having an accessible tab portion pullable to sever said collar member and remove it from said stopper, said disc-like member and said collar member being connected together whereby said disc-like member will separate from said stopper when said tab portion is pulled to sever said collar member.

7. The blood collection tube of claim 6 wherein said means forming a connection includes an adhesive.

8. The blood collection tube of claim 7 wherein said adhesive comprises a spot of adhesive between said disc-like cover member and collar member adjacent to said tab portion.

9. The blood collection tube of claim 6 wherein said plastic material is tearable, and said collar member includes at least one tear line of weakness at one side of said tab to facilitate tearing of said collar.

10. The blood collection tube of claim 6 wherein said tab portion extends below the lower edge of said collar member in normally space relation to said container.

11. The blood collection tube of claim 6 wherein said collar encircles and tightly fits only said stopper and said cover.

12. The medical container of claim 4 wherein said means forming a connection includes a spot of adhesive between said cover member and said collar adjacent said tab portion.

13. The medical container of claim 4 wherein said cover means includes a sidewall extending entirely around said peripheral surface of said external portion of said stopper, and an integral flange portion at the upper end of said sidewall extending entirely around said marginal portion of the exterior side of said cover member, and said tab portion is integrally connected to said sidewall and extends below said sidewall.

14. Closure means for a medical container having a stopper closing one end thereof comprising a cover member for positioning on the exterior end of the stopper, a collar member of shrinkable and severable material for shrinking onto the stopper with a portion thereof engageable with at least a portion of the exterior side of said cover member when on the stopper, said collar member having an accessible tab portion that can be pulled to sever said collar member to remove it from the stopper, and means for connecting said cover member with said collar member including a dot of adhesive positioned between said cover member and said collar member adjacent to aid tab portion whereby said cover member will separate from the stopper when said tab portion is pulled to sever said collar member.

* * * * *